United States Patent
Bankeström et al.

(10) Patent No.: US 6,708,128 B2
(45) Date of Patent: Mar. 16, 2004

(54) DEVICE, COMPUTER PROGRAM PRODUCT AND METHOD FOR INDICATING A FUNCTION DEVIATION OF ONE OR MORE DETAILS OF MANUFACTURING EQUIPMENT USING FREQUENCY COMPONENT ANALYSIS

(75) Inventors: Olle Bankeström, Frölunda (SE); Göran Gabrielsson, Särö (SE); Anders Göthberg, Lerum (SE)

(73) Assignee: Aktiebolaget SKF, Göteborg (SE)

(*) Notice: Subject to any disclaimer, the term of this patent is extended or adjusted under 35 U.S.C. 154(b) by 0 days.

(21) Appl. No.: 10/158,165

(22) Filed: May 31, 2002

(65) Prior Publication Data
US 2003/0016843 A1 Jan. 23, 2003

(51) Int. Cl.⁷ .................. G01R 23/16; G06F 19/00
(52) U.S. Cl. .................. 702/77; 702/75; 702/76; 702/183; 702/189
(58) Field of Search .................. 702/33, 34, 56, 702/57, 75–77, 80, 182, 183, 189, 190, 167–168; 73/579, 659, 660

(56) References Cited

U.S. PATENT DOCUMENTS

| | | |
|---|---|---|
| 4,048,849 A | 9/1977 | Gocho et al. |
| 4,084,324 A | 4/1978 | Whitehouse |
| 4,344,233 A | 8/1982 | Albertazzi |
| 4,425,798 A | 1/1984 | Nagai et al. |
| 4,453,407 A | 6/1984 | Sato et al. |
| 4,625,429 A | 12/1986 | Danielli |
| 5,022,267 A | 6/1991 | Shattuck et al. |
| 5,077,908 A | 1/1992 | Moore |
| 5,205,046 A | 4/1993 | Barnett et al. |
| 5,293,557 A | 3/1994 | Fujinaga et al. |
| 5,542,188 A | 8/1996 | Ertl et al. |
| 5,598,265 A | 1/1997 | de Groot |
| 5,870,699 A * | 2/1999 | Canada et al. .............. 702/190 |
| 5,978,750 A | 11/1999 | Adams |
| 6,062,948 A | 5/2000 | Schiff et al. |
| 6,385,553 B1 * | 5/2002 | Naito et al. .............. 702/138 |
| 6,494,046 B1 * | 12/2002 | Hayess .............. 60/779 |

FOREIGN PATENT DOCUMENTS

| | | |
|---|---|---|
| DE | 40 17 448 | 12/1990 |
| DE | 40 32 299 | 4/1992 |
| EP | 0 486 219 | 5/1992 |
| JP | 57-093229 A | 6/1982 |
| JP | 6-344246 A | 12/1994 |
| JP | 8-238551 A | 9/1996 |
| JP | 9-196657 A | 7/1997 |
| JP | 2001--280948 A | 10/2001 |
| JP | 2002-357409 A | 12/2002 |
| JP | 2003-098042 A | 4/2003 |
| JP | 2003-123073 A | 4/2003 |

* cited by examiner

*Primary Examiner*—Bryan Bui
(74) *Attorney, Agent, or Firm*—Burns, Doane, Swecker & Mathis, LLP (57) ABSTRACT

A device, method and computer program product are disclosed for indicating a function deviation of one or more details of manufacturing equipment using frequency component analysis for analyzing deviations between a nominal product shape and an actual product shape of a product using surface data of a physical surface, the product having been processed by the manufacturing equipment. The analysis can be based on the surface data and a set of function deviation indicating frequencies corresponding to frequencies at which function deviations occur in the one or more details. The function deviation indicating frequencies can be comprised in a frequency map. A method of configuring a frequency map is also disclosed.

22 Claims, 5 Drawing Sheets

| | Grinding Motor rpm | Grinding Motor Pulley Diameter | Grinding Spindle rpm | Grinding Spindle Pulley Diameter | Grinding Belt Length mm | Workhead Motor rpm | Workhead Motor Pulley Diameter | Ring Speed in rpm | Workhead Spindle Pulley Diameter | Workhead Belt Length mm | External Source Frequency | Full Profile Dresser rpm |
|---|---|---|---|---|---|---|---|---|---|---|---|---|
| | 1983,3 | 170,0 | 1750,0 | 150,0 | 2515,0 | 69,1 | 75,0 | 175,0 | 190,0 | 1210,0 | 15,0 | 3798,0 |

| Problem Area | No. of lobes | 1st Harmonics | 2nd Harmonics | 3rd Harmonics | 4th Harmonics | 5th Harmonics | 6th Harmonics | 7th Harmonics | 8th Harmonics | 9th Harmonics | 10th Harmonics | 11th Harmonics |
|---|---|---|---|---|---|---|---|---|---|---|---|---|
| Grinding Motor Pulley Unbalance | 11,33 | 22,67 | 34,00 | 45,33 | 56,67 | 68,00 | 79,33 | 90,67 | 102,00 | 113,33 | 124,66 | 136,00 |
| Grinding Wheel Pulley Unbalance | 10,00 | 20,00 | 30,00 | 40,00 | 50,00 | 60,00 | 70,00 | 80,00 | 90,00 | 100,00 | 110,00 | 120,00 |
| Belt Quality Grinding side | 2,41 | 4,81 | 7,22 | 9,63 | 12,03 | 14,44 | 16,85 | 19,25 | 21,66 | 24,07 | 26,47 | 28,88 |
| Work Head Motor, Pulley Unbalance | 0,39 | 0,79 | 1,18 | 1,58 | 1,97 | 2,37 | 2,76 | 3,16 | 3,55 | 3,95 | 4,34 | 4,74 |
| Dresser Runout / Balance | 21,70 | 43,41 | 65,11 | 86,81 | 108,51 | 130,22 | 151,92 | 173,62 | 195,33 | 217,03 | 238,73 | 260,43 |
| External Source Problem | 5,14 | 10,29 | 15,43 | 20,57 | 25,71 | 30,86 | 36,00 | 41,14 | 46,29 | 51,43 | 56,57 | 61,71 |

Fig. 6

DEVICE, COMPUTER PROGRAM PRODUCT AND METHOD FOR INDICATING A FUNCTION DEVIATION OF ONE OR MORE DETAILS OF MANUFACTURING EQUIPMENT USING FREQUENCY COMPONENT ANALYSIS

This application is based on and claims priority under 35 U.S.C. §119 with respect to Swedish Patent Application No. 0101984-3 filed on May 31, 2001, the entire content of which is incorporated herein by reference.

FIELD OF THE INVENTION

The present invention relates to a device, computer program product and method for indicating a function deviation of one or more details of manufacturing equipment using frequency component analysis for analyzing deviations from a nominal product shape and an actual product shape using surface data of a physical surface describing the present product shape, the product having been processed by the manufacturing equipment. It also relates to a device for indicating the quality of a product processed by the manufacturing equipment.

The invention also relates to a method of configuring a frequency map comprising a set of function deviation indicating frequencies, the map being intended to be used in a device for indicating a function deviation of one or more details of a manufacturing equipment.

BACKGROUND OF THE INVENTION

One way of obtaining indications of whether there are problems in manufacturing equipment is to use a vibration sensor to sense vibrations of the manufacturing equipment. A frequently used method of analyzing the vibrations is based on the Fourier analysis.

In U.S. Pat. No. 4,453,407 to Sato et al., assigned on its face to Hitachi, a vibration diagnosis method and apparatus for rotary machines are presented. It is adapted for measuring the vibration of a rotor shaft of a rotary machine, extracting the vibration component synchronous with the revolution of the rotor shaft from the measured vibration data, comparing the amplitude of the extracted vibration component with the amplitude of the overall vibration, analyzing the causes of the synchronous vibration component when the result of the comparison meets a predetermined reference, judging, in accordance with the result of the analysis, whether the vibration due to mass unbalance is attributable to an abrupt generation of mass unbalance or to a thermal bow of the rotor shaft, and displaying the result of the judgment.

In U.S. Pat. No. 4,425,798 to Nagai et al., assigned on its face to Kawasaki Steel, an apparatus for diagnosing abnormalities in rotating machines is presented. It is intended to be used for the diagnosis of rotary machinery equipment and utilizes a fast Fourier transform frequency spectrum analysis system. The presence or absence of an abnormality or trouble in the rotating machinery is determined by selecting high amplitudes out from the frequency spectrum computed by the FFT frequency spectrum analysis system, arithmetically processing distribution data of spectrum amplitudes adjacent each frequency giving the corresponding high amplitude, and detecting the amplitude, at which the frequency of vibrations of the rotating machinery has attained a maximum value, together with such a frequency.

In the fields of diagnosing and monitoring machinery equipment, Fourier analysis has been used as disclosed in DE 40 17 448 A1 and DE 40 32 299 A1.

Approaches of the kinds presented above are intended to be used to diagnose machinery equipment so that they do not malfunction and start to machine products of too low quality. A common feature of the inventions disclosed in the documents above is that the diagnosis is based on vibrations detected by sensors.

It has been realized that there are a lot of vibrations in machinery equipment to be detected by these sensors and that not all of the vibrations that can be detected in a machinery equipment lead to products of too low quality. This means that there are vibrations in machinery equipment that do not jeopardize the quality of the product. Since not all vibrations impede the quality of the product there is a risk that the presence of harmless vibrations makes it difficult to detect harmful vibrations.

Thus, it has been realized that measuring vibrations using vibration sensors on machinery equipment can lead to the disadvantage of having to deal with vibrations that do not effect the quality of the product being machined.

SUMMARY OF THE INVENTION

According to one aspect of the present invention, there is provided a device for indicating a function deviation of one or more details of manufacturing equipment using frequency component analysis. An example of a detail is a pulley, which is arranged in manufacturing equipment. Other examples of details will be presented below. The frequency component analysis can be used to analyze deviations between a nominal product shape and an actual product shape of a product using surface data of a physical surface describing the actual product shape, the product having been processed by the manufacturing equipment. The nominal product shape is the shape of a product if it had been manufactured in a perfect machine with no limitations when it comes to precision. It can also be seen as the 'theoretical' shape. The actual product shape (or present product shape) is the shape the product actually has. This shape is likely to vary between products intended to have the same nominal shape. It can be seen as the 'practical' shape.

The analysis can be based on the surface data and a set of function deviation indicating frequencies corresponding to frequencies at which function deviations occur in the one or more details. The function deviation frequencies can be comprised in a frequency map.

The device comprises an input connection, a memory comprising the frequency map, an indicator, and a computational means for receiving the surface data via the input connection, performing a Fourier transformation of the surface data, and indicating, using the indicator, the correspondence between the frequency components of the surface data and the function deviation indicating frequencies of the frequency map. These steps are responsive for performing the actual indication of a function deviation.

Analyzing how the actual product shape of a product having been processed by the manufacturing equipment varies in relation to the nominal product shape can be used as an indication of the state of the manufacturing equipment.

Surface data of a physical surface of the actual product shape describes the present (actual) product shape as it as been processed by the manufacturing equipment.

The surface data can originate from an actual surface of a rotational surface or a plane surface, for example.

Analyzing the product processed by the manufacturing equipment is advantageous since only the frequencies that affect the actual product shape is detected. This means that vibrations not resulting in a change of the actual product shape do not impede the indication. Also, it is not necessary to test every product to see whether there are problems in the manufacturing equipment. It is sufficient to test only a fraction of the products processed by a the equipment. This means that the present invention does not have to be used on a continuous basis. Another advantage is that a product can be analyzed after it has been manufactured. With other solutions this is not possible since the vibration data is normally not present at later times. This is because the Fourier analyses of other approaches are based on time directly, but in the present invention the Fourier analysis is based on a mark or a deviation of the actual product shape. Thus there is a spatial aspect of the Fourier analysis as suggested in the present invention.

Exemplary details of manufacturing equipment are details operating with frequencies, including overtones for rotating equipment within the manufacturing equipment, such as a rotary shaft, drive motor and belts. For instance, if a belt has become worn, the present invention will indicate that a function deviation has occurred, provided that there is an effect on the products manufactured by the manufacturing equipment. One feature of relevance here is relationships of revolutions of one detail and effects of these revolutions on other details within the manufacturing equipment.

The analysis can be based on the surface data of the actual product shape and a set of function deviation indicating frequencies corresponding to frequencies at which function deviations occur in the one or more details of the manufacturing equipment. This leads to an advantage of being able to indicate a probable cause of the deviation in the actual product shape. The function deviation indicating frequencies can be comprised in a frequency map.

In one embodiment the computational means can be further configured for comparing frequency components of the surface data with the function deviation indicating frequencies of the frequency map and for indicating, using the indicator, in case a correspondence is detected between at least one frequency of the set of function deviation indicating frequencies of the frequency map and at least one frequency component of the surface data. After indication, the function deviation can be further examined and later alleviated so that the manufacturing equipment can go back to its normal working conditions.

In another embodiment the correspondence can be arranged to be based on the correlation between the frequency components of the surface data and the function deviation indicating frequencies of the frequency map. Thus, for example, a correlation exceeding a predetermined level leads to an indication that the presence of a function deviation has occurred. By analyzing what frequency component is responsible for the indication the function deviation can be found and alleviated.

According to another embodiment the surface data can correspond to a line along the surface of the product. In one example, the line can have an orientation in a processing direction of the manufacturing equipment. In another example, the line can have an orientation in which at least a component of the line is in the processing direction of the manufacturing equipment.

Situations in which a line is in the processing direction can be found, for instance, in paper mills and rolling mills, in which paper and steel are manufactured in the processing direction. In some cases the line is not limited to being in the processing direction of the product. However, the line should comprise a vector component that covers the variation of the surface to be measured and analyzed. Also that vector component must be able to be isolated. For instance, a line being sampled diagonally in relation to a processing direction over a nominal flat surface can be seen as comprising two vector components: one in the processing direction and one in a perpendicular direction. Depending on what vector is of interest, a proper one can be chosen and subjected to Fourier transformation.

In one embodiment the surface data can be in the form of two-dimensional surface data of the physical surface to be analyzed. In this case the computational means can be further configured for forming one dimensional surface data from the two dimensional surface data, i.e. to select data forming a line along the surface. This offers the advantage that from a sample of a physical surface it is possible to form more than one line which results in increased opportunities of performing more than one frequency analysis using the present invention.

In another embodiment the surface data can be one dimensional and can be transferred using a one dimensional Fourier transform. In another embodiment the surface data can be two dimensional and can be transformed using a two dimensional Fourier transform.

In another embodiment the device can be configured to be portable or stationary. A portable device is advantageous when performing on site analysis, and a stationary device is advantageous when used in a competence center.

In another embodiment the Fourier transformation can be one of the fast type and the continuous type. Today, in the digital world, the fast Fourier analysis is advantageous but it should be pointed out that the continuous Fourier transform can be employed to fully reach the potentials of the present invention. It should also be noted that the present invention can be carried out by combining analogue and digital electronics. For instance, a specially designed electronic circuit may be employed to send an output signal to a computer screen for indicating presence of a function deviation.

In another embodiment the computational means can be a digital computer.

In another embodiment the frequency map can be comprised in a memory located at one location, the computational means can be located at another location, and the memory and the computational means can be interconnected by a computer network. This opportunity offers the advantage of having frequency maps at different levels 1) a manufacturing unit; 2) a set of manufacturing units of a plant; 3) a set of manufacturing units of a company.

A computer network offers an opportunity of analyzing manufacturing units at a location distant from the memory. This is advantageous when assessing the condition of manufacturing equipment.

In another embodiment the input connection can be coupled to a communication network. This facilitates the opportunity of obtaining surface data electronically. This is advantageous since time is saved using this option. Also, this is advantageous since this means that the analysis does not have to be performed on site. It can also be performed on an aggregate level.

In another embodiment the input connection can be coupled to a disk drive station of a computer. This facilitates the opportunity of obtaining surface data on a disk. This is advantageous since this means that the analysis does not have to be performed on site.

An alternative use of the present invention is to use it to indicate the quality of the product. However this does not require the use of the frequency map but only the frequency components that indicate the physical surface of the actual product shape. This offers the advantage of obtaining information concerning the quality of the product.

The present invention can be used with different kinds of manufacturing equipment, for instance in manufacturing equipment for grinding, hot rolling, cold rolling, turning, milling, printing, polishing, and honing.

According to one embodiment the indicator can comprise a computer screen. Thus, when the device detects a function deviation in a product machined by the manufacturing equipment, the device can indicate this using the computer screen.

According to another embodiment the indicator can comprise an alarm. Thus, when the device detects a function deviation in a product machined by the manufacturing equipment, the device can indicate this by sending an alarm.

According to another aspect of the present invention, there is provided a method for indicating a function deviation of one or more details of manufacturing equipment. The method can be carried out, for example, using a device comprising an input connection, a memory comprising a frequency map, an indicator, and a computational means. The method can use frequency component analysis for analyzing deviations between a nominal product shape and an actual product shape of a product using surface data of a physical surface describing the actual product shape, the product having been processed by the manufacturing equipment. The analysis can be based on the surface data and a set of function deviation indicating frequencies corresponding to frequencies at which function deviations occur in the one or more details, the function deviation indicating frequencies being comprised in a frequency map. The method comprises receiving the surface data, e.g., via the input connection, performing a Fourier transformation of the surface data, and indicating, e.g., using the indicator, the correspondence between the frequency components of the surface data and the frequency map.

In addition, the method can further comprise comparing the frequency components of the surface data with the frequency map, and indicating in case a correspondence is detected between at least one frequency of the set of function deviation indicating frequencies of the frequency map and at least one frequency component of the surface data.

The method can be performed either on site or at a distant location, for instance, at a so called competence center.

According to another aspect of the present invention, there is provided a computer program product, which is loadable into the internal memory of a computer, comprising software code portions for performing the steps of the above-noted method, when run on a computer. This aspect facilitates the opportunity of using a general purpose computer, a PC, to perform the analysis. Distributing computer software today, can for instance be done by distributing a carrier, such as a CD-ROM, which is one embodiment of this aspect of the present invention. Computer software can also be distributed from an Internet web-site from which it is possible to download the computer program product. Thus, a computer program product can comprise, for example, a carrier, such as a CD-ROM, or a downloadable set of computer instructions that can cause a computer to perform the steps of the above noted method.

According to another aspect of the present invention, there is provided a method for indicating a function deviation of one or more details of manufacturing equipment using frequency component analysis for analyzing deviations between a nominal product shape and an actual product shape of a product using surface data of a physical surface describing the actual product shape, the product having been processed by the manufacturing equipment. The analysis can be based on the surface data and a set of function deviation indicating frequencies corresponding to frequencies at which function deviations occur in the one or more details. The function deviation indicating frequencies can be comprised in a frequency map. The method comprises receiving the surface data, performing a Fourier transformation of the surface data, comparing frequency components of the surface data with the frequency map, and indicating a correspondence between the frequency components of the surface data and the frequency map. An advantage of this aspect is that, in cases where the test frequency of products manufactured by the manufacturing equipment is low, the need of having an electronic device indicating manufacturing equipment status using a product manufactured by the manufacturing equipment is lower, perhaps even obsolete, since the actual indicating can be achieved using a lower level of electronic presence.

According to another aspect of the present invention a method of configuring a frequency map of a memory is disclosed. The frequency map comprises a set of function deviation indicating frequencies. The map is intended to be used in a device for indicating a function deviation of one or more details of a manufacturing equipment. The method comprises investigating function deviation indicating frequencies occurring in the manufacturing equipment, and inputting relevant function deviation indicating frequencies into the memory.

The investigation step can comprise scanning the manufacturing equipment for details that can produce function deviation indicating frequencies, and setting numerical values to the function deviation indicating frequencies of the details. These latter steps can be performed, for example, by an individual.

The information that is necessary to perform these steps can be found, for instance, in product manuals and maintenance manuals. Alternatively, this information can be obtained by an on-site investigation of the manufacturing equipment.

BRIEF DESCRIPTION OF THE DRAWING FIGURES

The foregoing and additional features and characteristics of the present invention will become more apparent from the following detailed description considered with reference to the accompanying drawing figures in which like reference numerals designate like elements.

DESCRIPTION OF THE INVENTION

Figure 1:
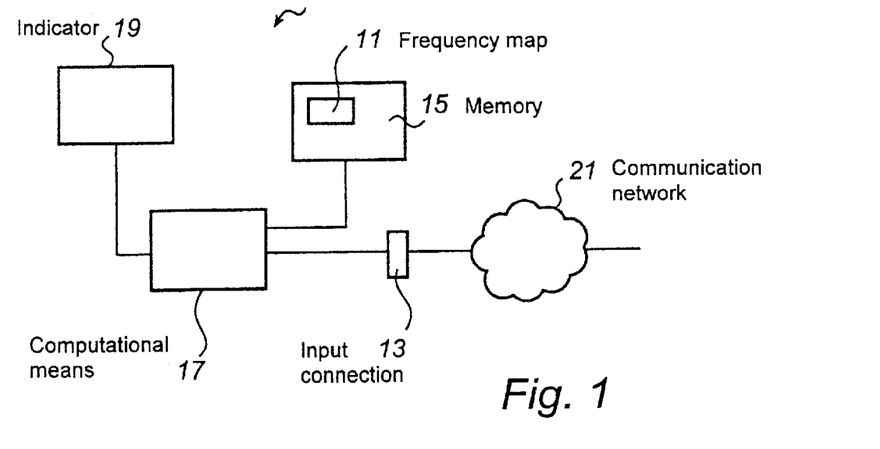
FIG. 1 schematically shows an exemplary device for indicating a function deviation of one or more details of manufacturing equipment using frequency component analysis.

In FIG. 1 a device 1 for indicating a function deviation of one or more details of manufacturing equipment is disclosed according to a first exemplary aspect of the present invention. The function of the device 1 is based on frequency component analysis for analyzing deviations between a nominal product shape and an actual product shape of a product. The input to the device 1 is surface data 3 of a physical surface 5, such as shown in FIGS. 2 and 3, describing the present (actual) product shape.

Figure 2:
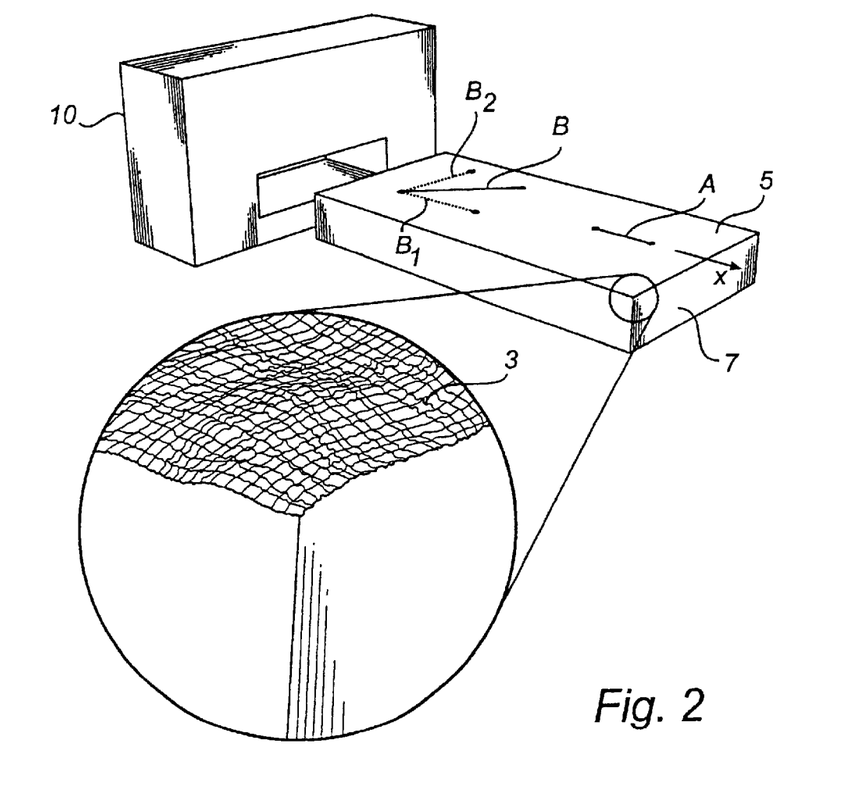
FIG. 2 schematically illustrates, for example, a portion of a paper in a paper manufacturing process or a sheet of iron at a rolling plant as well as an enlarged detailed view of a portion of the paper or iron sheet.
Figure 3:
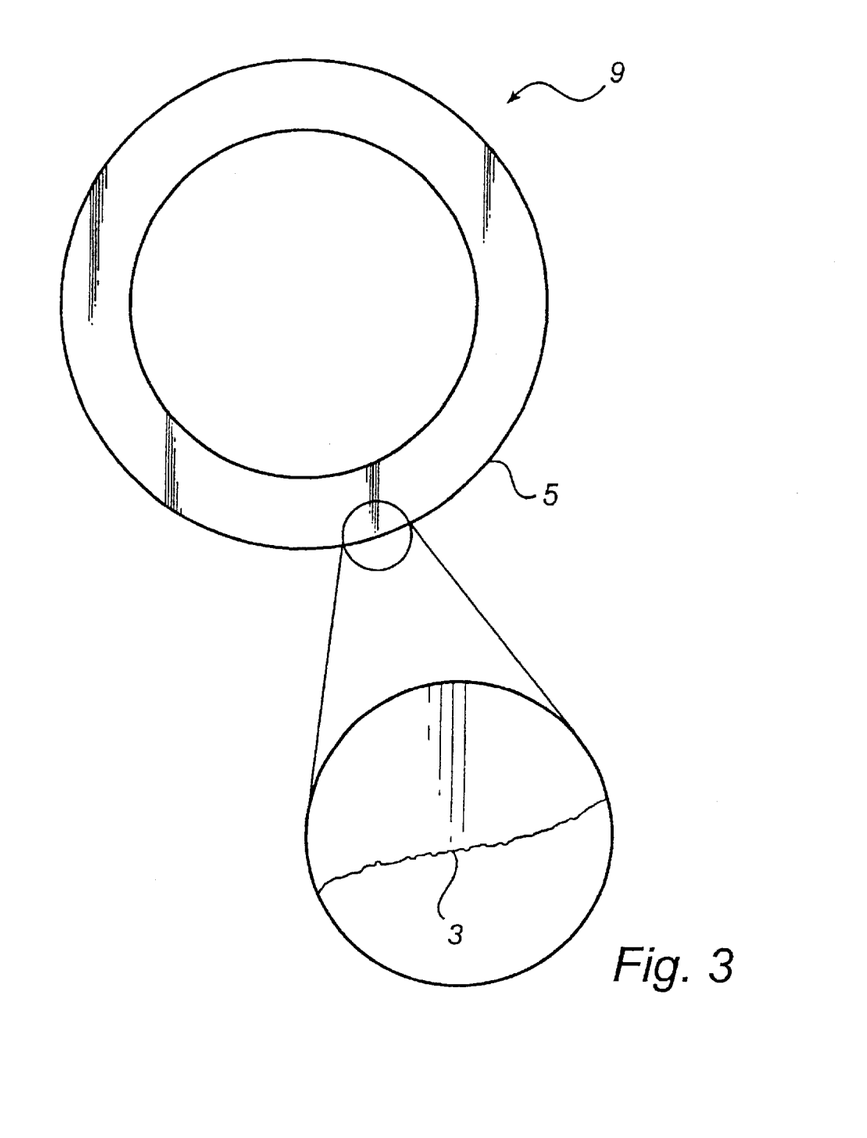
FIG. 3 schematically illustrates a bearing ring as well as an enlarged detailed view of a portion of the bearing ring illustrating waviness of the outer surface of a bearing ring.

Examples of a physical surface 5 and physical surface data 3 are presented in FIGS. 2 and 3. One interpretation of the embodiment presented in FIG. 2 is that the surface data 3 originates from a plane surface, for example, a sheet of iron 7. Another interpretation of the embodiment presented in FIG. 3 is that the surface data 3 originates from a rotational surface, for example, the outer surface of a bearing ring 9. FIG. 3 schematically presents a bearing ring 9 of which the physical surface of the outside of the ring 9 exhibits a waviness. In FIG. 3 the waviness is emphasized for purposes of illustration.

One notion is that a product having been processed by the manufacturing equipment 10 constitutes the foundation of the analysis since the analysis is based on the surface data 3 of the product 7 (or 9), such as shown in FIGS. 2 and 3. Frequency components of the surface data 3 can be compared to a set of function deviation indicating frequencies. These function deviation indicating frequencies correspond to frequencies at which function deviations occur in the one or more details of the manufacturing equipment. The function deviation indicating frequencies can be comprised in a frequency map 11.

Exemplary details include details operating with frequencies, including overtones for rotating equipment within the manufacturing equipment 10, such as a rotary shaft, a pulley, a drive motor and belts. One feature of relevance here is relationships of revolutions of one detail and effects of these revolutions on other details within the manufacturing equipment.

The device 1 comprises an input connection 13, a memory 15 comprising the frequency map 11, a computational means 17, which can be, for example, a digital computer, and an indicator 19. The computational means 17 is configured for receiving the surface data 3 via the input connection 13, performing a Fourier transformation of the surface data 3, and indicating, using the indicator 19, the correspondence between the frequency components of the surface data 3 and the function deviation indicating frequencies of the frequency map 11.

In addition, the computational means 17 can be configured for comparing frequency components of the surface data 3 with the function deviation indicating frequencies of the frequency map 11, and for indicating, using the indicator 19, in case a correspondence is detected between at least one frequency of the set of function deviation frequencies of the frequency map 11 and at least one frequency component of the surface data 3.

In one embodiment, the correspondence can be arranged to be based on a correlation between the frequency components of the surface data and the function deviation indicating frequencies of the frequency map.

If the waviness of the exemplary surfaces presented in FIGS. 2 and 3 correspond to a frequency of the frequency map 11, this is interpreted and indicated as a function deviation.

Figure 4:
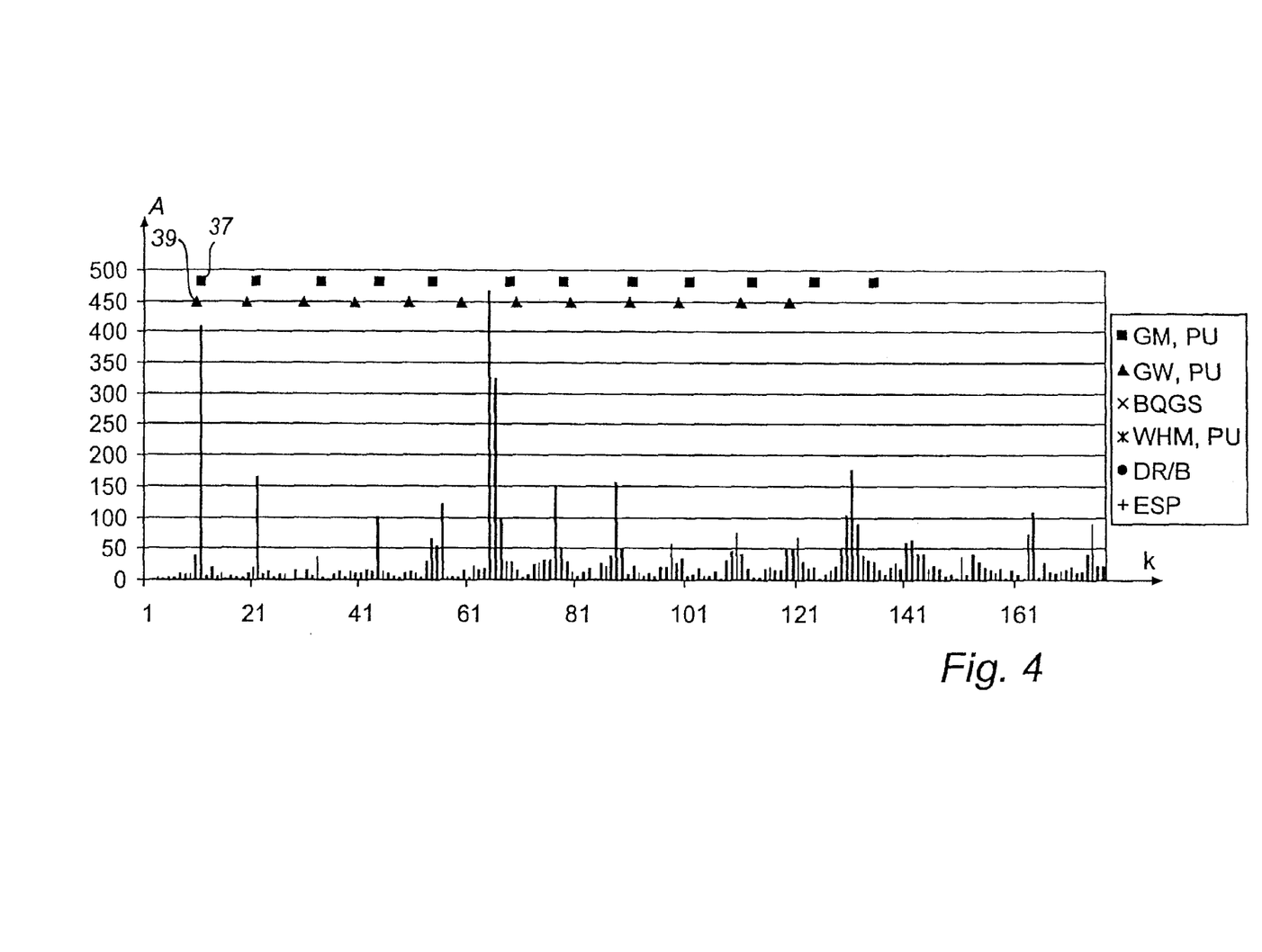
FIG. 4 shows exemplary frequency components of a surface having been analyzed.

In one embodiment the indication can be presented as shown in FIG. 4, for example. From the information presented in FIG. 4 a user can draw conclusions that the presence of function deviation affecting the product has occurred in the manufacturing equipment 11.

In another embodiment of the present invention the indicator 19 can comprise a computer screen.

In an alternative embodiment of the present invention the indicator 19 can comprise an alarm arranged for notification.

The surface data 3 can correspond to data of a physical surface 5 forming a line along a surface of the product.

In one embodiment the line, such as line A presented in FIG. 2, for example, is oriented in the processing direction X of the manufacturing equipment 10.

In another embodiment the line has an orientation in which at least a component of the line is in the processing direction X of the manufacturing equipment. As shown in FIG. 2, for example, the components of the line B are the two components $B_1$ and $B_2$. The component $B_1$ is in the manufacturing process direction.

In one embodiment the surface data 3 can be one dimensional and a one dimensional fast Fourier transform can be employed to transform the surface data. However, in an alternative embodiment the surface data 3 of the product presented in FIG. 2 can be two dimensional, and a two dimensional Fourier transform can be employed to transform the surface data. In yet another alternative embodiment the surface data 3 can be in the form of two-dimensional surface data 5, and the computational means 17 can be arranged for forming one dimensional surface data, preferably in the form of a straight line, from the two dimensional surface data.

FIG. 4 presents the indication of the condition of the manufacturing equipment 10 in terms of presence of function deviations. In FIG. 4, the waviness amplitude, A, is presented in relation to the wave order, marked k. In FIG. 4 the function deviation frequencies, are also presented. However, they are presented in the wave order form. The data in FIG. 4 will be further discussed below. In the exemplary embodiment presented in FIG. 4 the indicator 19 is constituted by a computer screen.

In one embodiment the input connection 13 can be coupled to a communication network 21. In another embodiment the input connection 13 can be coupled to a disk drive station of a computer, which is not shown in FIG. 1. In another embodiment, the frequency map 11 can be comprised in a memory 15 located at one location, and the computational means 17 can be located at another location. The memory 15 and the computational means 17 can be interconnected by a computer network.

In one embodiment the device 1 can be arranged to be portable. In another embodiment, the device 1 can be arranged to be stationary.

In addition, the physical surface 5, from which the surface data 3 is obtained, can be formed by at least one of grinding, hot rolling, cold rolling, turning, milling, printing, polishing and honing, for example. In addition, the device 1 can be configured to indicate the quality of the product.

In another embodiment the correspondence can arranged to be based on the correlation between the frequency components of the surface data and the function deviation indicating frequencies of the frequency map. Thus, a correlation exceeding a predetermined level leads to an indication that the presence of a function deviation has occurred. By analyzing what frequency component is responsible for the indication, the function deviation can be found and alleviated.

According to another aspect of the present invention, there is provided a method for indicating a function deviation of one or more details of manufacturing equipment. The method can be carried out, for example, using a device comprising an input connection 13, a memory 15 comprising a frequency map 11, a computational means 17, and an indicator 19, such as illustrated in FIG. 1. The method can use frequency component analysis for analyzing deviations between a nominal product shape and an actual product shape of a product using surface data 3 of a physical surface describing the actual product shape, the product having been processed by the manufacturing equipment. The analysis can be based on the surface data 3 and a set of function deviation indicating frequencies corresponding to frequencies at which function deviations occur in the one or more details, the function deviation indicating frequencies being comprised in a frequency map 11. The method comprises receiving the surface data 3, e.g., via the input connection 13, performing a Fourier transformation of the surface data 3, and indicating, e.g., using the indicator 19, the correspondence between the frequency components of the surface data 3 and the frequency map 11.

In addition, the method can further comprise comparing the frequency components of the surface data 3 with the frequency map 11, and indicating in case a correspondence is detected between at least one frequency of the set of function deviation indicating frequencies of the frequency map 11 and at least one frequency component of the surface data 3.

In another aspect of the present invention, there is provided a computer program product loadable into the internal memory of a computer, comprising software code portions for performing the steps of the above-noted method, when run on a computer. This aspect facilitates the opportunity of using a general purpose computer, a PC, to perform the analysis. Distributing computer software today, can be done, for example, by distributing a carrier, such as a CD-ROM, which is one embodiment of this aspect of the present invention. Computer software can also be distributed from an Internet web-site from which it is possible to download the computer program product. Thus, a computer program product can comprise, for example, a carrier, such as a CD-ROM, or a downloadable set of computer program instructions that can cause a computer to perform the steps of the above-noted method.

According to another aspect of the present invention, there is provided a method of configuring a frequency map 11 of a memory 15 comprising a set of function deviation indicating frequencies, the memory 15 being comprised in a device 1 for indicating a function deviation of one or more details of manufacturing equipment. Frequency component analysis can be used for analyzing deviations between a nominal product shape and an actual product shape of a product using surface data 3 of a physical surface describing the actual product shape, the product having been processed by the manufacturing equipment 10. The analysis can be based on the surface data 3 and a set of function deviation indicating frequencies corresponding to frequencies at which function deviations occur in the one or more details. The method comprises investigating function deviation indicating frequencies occurring in the manufacturing equipment 10, and inputting the relevant function deviation indicating frequencies into the memory 15.

In one embodiment the step of investigating can comprise scanning the manufacturing equipment 10 for details that can produce function deviation indicating frequencies, and setting numerical values to the function deviation indicating frequencies of the details.

Figure 5:
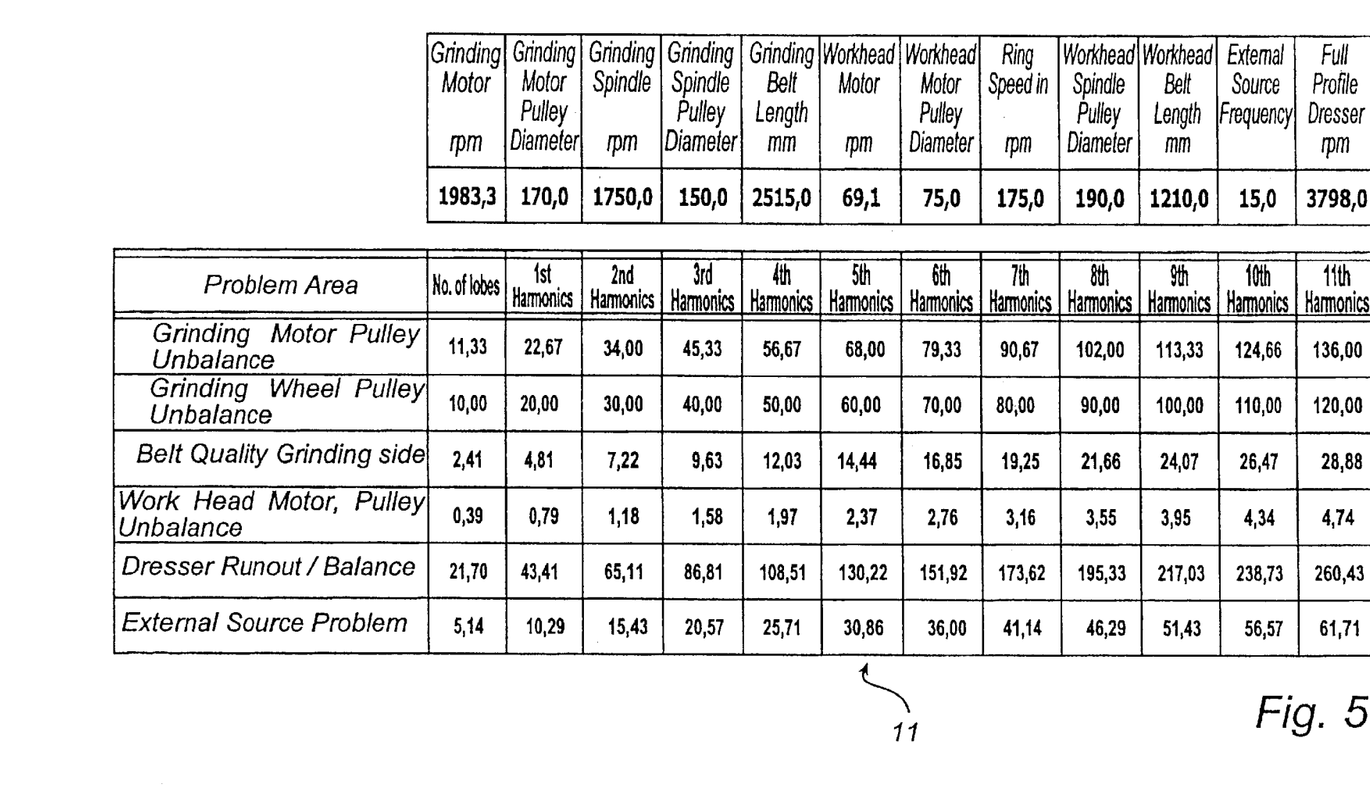
FIG. 5 shows an exemplary frequency map.

An example showing the procedure of configuring the frequency map 11 will now be given. In FIG. 5 an embodiment of a frequency map 11 is presented. At the top there is a number of names of details presented in connection of numerical values of operating parameters, for instance, 'Grinding motor (rpm)'. On the left, a number of problem areas are listed, for instance, 'Grinding Motor Pulley Unbalance'. To the right of the problem areas shown in FIG. 5, the function deviation frequencies are listed. In this example, the function deviation frequencies are provided in the form of the number of lobes. The function deviation frequencies of the details of manufacturing equipment 10 listed at the top of FIG. 5 are shown for a specific application. FIG. 5 also includes the harmonics, which are presented in relation to the number of lobes.

In an exemplary embodiment of specific relationships between operating parameters, e.g. 'Grinding Motor', and different problem areas, e.g. 'Grinding Motor, Pulley Unbalance', a number of formulas are presented below in Table 1. Of course, these formulas are not intended to be limiting in any way. In view of this example, one of ordinary skill in the art will be able to devise appropriate formulas for calculating the number of lobes for any given manufacturing equipment for a given application.

TABLE 1

| Problem area | Formula for calculating no. of lobes |
| --- | --- |
| Grinding motor, Pulley unbalance | (rpm of grinding motor)/(rpm of ring speed) |
| Grinding wheel, Pulley unbalance | (rpm of grinding spindle)/(rpm of ring speed) |
| Belt quality grinding side | (rpm of grinding motor) · (grinding motor pulley diameter) · PI/((grinding belt length) · (rpm of ring speed)) |
| Work head motor, Pulley unbalance | (rpm of work head motor)/(rpm of ring speed) |
| Dresser run out/Balance | (rpm of full profile dresser)/(rpm of ring speed) |
| External source problem | 60 · (external source frequency)/(rpm of ring speed) |

Figure 6:
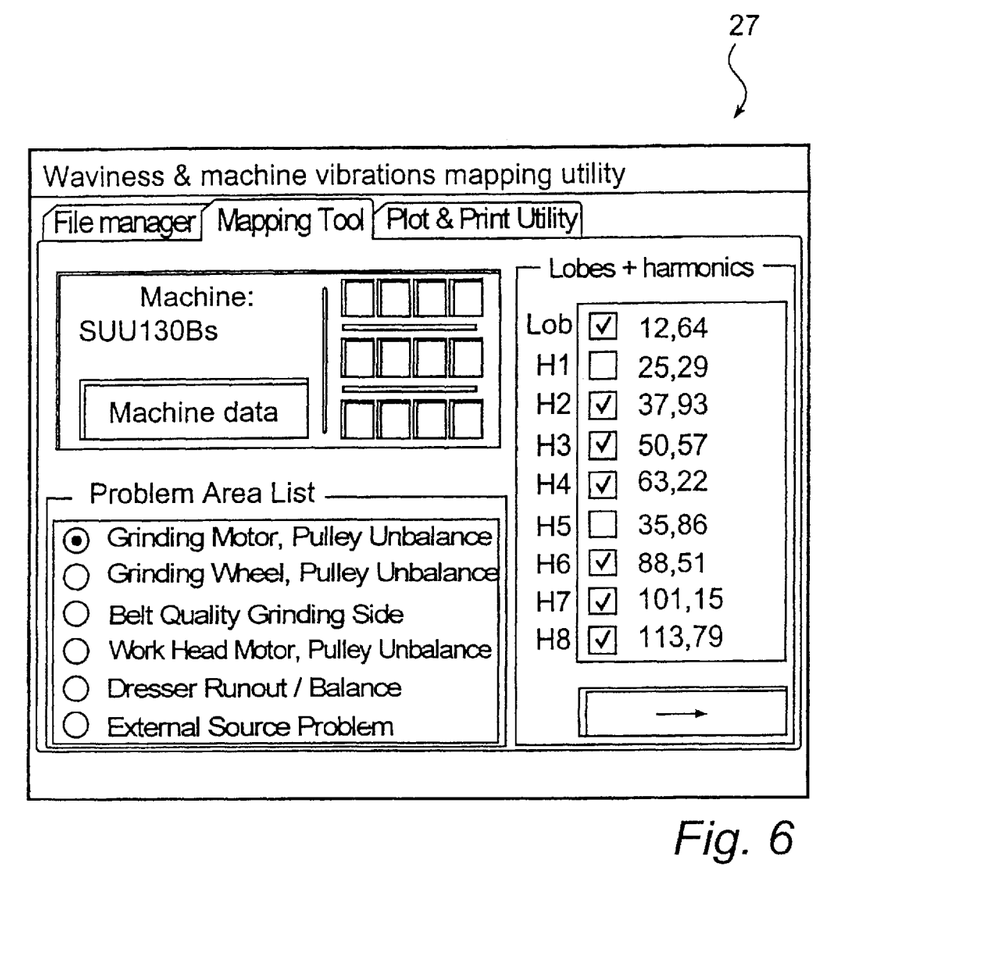
FIG. 6 shows exemplary aspects of a computer interface useful when configuring the frequency map.

In FIG. 6 an example of a computer interface 27 for managing the function deviation frequencies, lobes and harmonics, is presented. By clicking an item of the problem area, a list the function deviation frequencies, lobes and harmonics can be presented.

The numbers of lobes and their harmonics presented in FIG. 5 are interpreted in FIG. 4. In FIG. 4 the numbers of lobes and overtones/harmonics indicating function deviation problem areas shown in FIG. 5 are illustrated according to the abbreviations in the legend of FIG. 4. Table 2 below presents the abbreviations and their associated problem areas.

TABLE 2

| Problem area | Abbreviation |
| --- | --- |
| Grinding motor, Pulley unbalance | GM, PU |
| Grinding wheel, Pulley unbalance | GW, PU |
| Belt quality grinding side | BQGS |
| Work head motor, Pulley unbalance | WHM, PU |
| Dresser run out/Balance | DR/B |
| External source problem | ESP |

It should be noted that only the function deviation frequencies of the frequency map 11 related to 1) Grinding motor, Pulley unbalance and 2) Grinding wheel, Pulley unbalance are presented in FIG. 4.

In FIG. 4 the function deviation frequencies related to the problem area of Grinding Motor, Pulley Unbalance are indicated using black boxes 37. All in all, there are 12 black boxes 37 in relation to the k axis shown in FIG. 4. The locations of the black boxes 37 correspond to the contents of FIG. 5.

In FIG. 4 the function deviation frequencies related to the problem area of Grinding Wheel, Pulley Unbalance are indicated using black triangles 39. All in all, there are 12 triangles shown in FIG. 4. The locations of the triangles 39 in relation to the k axis correspond to the contents of FIG. 5.

For purposes of clarity, the indications of other function deviation frequencies (Belt quality grinding side, Work head motor, Pulley unbalance, Dresser run out/Balance, and External source problem) are not included in FIG. 4.

According to another aspect of the present invention, there is provided a method for indicating a function deviation of one or more details of manufacturing equipment. The method can be carried out, for example, using a device comprising an input connection 13, a memory 15 comprising a frequency map 11, a computational means 17, and an indicator 19, such as illustrated in FIG. 1. The method can use frequency component analysis for analyzing deviations between a nominal product shape and an actual product shape of a product using surface data 3 of a physical surface describing the present product shape, the product having been processed by the manufacturing equipment. The analysis can be based on the surface data and a set of function deviation indicating frequencies corresponding to frequencies at which function deviations occur in the one or more details, the function deviation indicating frequencies being comprised in a frequency map 11. The method comprises receiving the surface data 3, e.g., via the input connection 13, performing a Fourier transformation of the surface data 3, comparing frequency components of the surface data 3 with the frequency map 11, and indicating in case a correspondence is detected between at least one frequency of the set of function deviation indicating frequencies of the frequency map and at least one frequency component of the surface data. An advantage of this aspect is that, in cases where the test frequency of products manufactured by the manufacturing equipment is low, the need of having an electronic device indicating manufacturing equipment status using a product manufactured by the manufacturing equipment is lower, perhaps even obsolete, since the actual indicating can be achieved using a lower level of electronic presence.

Principles, embodiments and modes of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims be embraced thereby.

What is claimed is:

1. A device for indicating a function deviation of one or more details of manufacturing equipment using frequency component analysis for analyzing deviations between a nominal product shape and an actual product shape of a product using surface data of a physical surface describing the actual product shape, the product having been processed by the manufacturing equipment, the analysis being based on the surface data and a set of function deviation indicating frequencies corresponding to frequencies at which function deviations occur in the one or more details, the function deviation indicating frequencies being comprised in a frequency map, the device comprising:

an input connection;

a memory comprising the frequency map;

an indicator; and computational means for receiving the surface data via the input connection, performing a Fourier transformation of the surface data, and indicating, using the indicator, a correspondence between frequency components of the surface data and the function deviation indicating frequencies of the frequency map.

2. A device according to claim 1, in which the computational means is further configured for:

comparing frequency components of the surface data with the function deviation indicating frequencies of the frequency map, and indicating, using the indicator, in case a correspondence is detected between at least one frequency of the set of function deviation indicating frequencies of the frequency map and at least one frequency component of the surface data.

3. A device according to claim 2, wherein the indicator comprises an alarm.

4. A device according to claim 1, wherein the surface data corresponds to a line along the surface of the product, the line having one of:

an orientation in a processing direction of the manufacturing equipment, and an orientation in which at least a component of the line is in the processing direction of the manufacturing equipment.

5. A device according to claim 1, wherein the surface data are one of:

one dimensional wherein the surface data are transformed using a one dimensional Fourier transform; and two dimensional wherein the surface data are transformed using a two dimensional Fourier transform.

6. A device according to claim 1, wherein the surface data are in the form of two-dimensional surface data of the physical surface, and the computational means is further configured for forming one dimensional surface data from the two dimensional surface data.

7. A device according to claim 1, wherein the surface data originates from one of:

a rotational surface, and a plane surface.

8. A device according to claim 1, wherein the indicator comprises a computer screen.

9. A device according to claim 1, wherein the input connection is coupled to a communication network.

10. A device according to claim 1, wherein the input connection is coupled to a disk drive station of a computer.

11. A device according to claim 1, wherein the device is further configured to indicate a quality of the product.

12. A device according to claim 1, wherein the physical surface, from which the surface data is obtained, is formed by at least one of grinding, hot rolling, cold rolling, turning, milling, printing, polishing, and honing.

13. A device according to claim 1, wherein the device is arranged to be one of portable and stationary.

14. A device according to claim 1, wherein the computational means is a digital computer.

15. A device according to claim 1, wherein the frequency map is comprised in a memory located at one location and the computational means is located at another location, the memory and the computational means being interconnected by a computer network.

16. A device according to claim 1, wherein the correspondence is arranged to be based on a correlation between the frequency components of the surface data and the function deviation indicating frequencies of the frequency map.

17. A method for indicating a function deviation of one or more details of manufacturing equipment using frequency component analysis for analyzing deviations between a nominal product shape and an actual product shape of a product using surface data of a physical surface describing the actual product shape, the product having been processed by the manufacturing equipment, the analysis being based on the surface data and a set of function deviation indicating frequencies corresponding to frequencies at which function deviations occur in the one or more details, the function deviation indicating frequencies being comprised in a frequency map, the method comprising:

receiving the surface data;

performing a Fourier transformation of the surface data; and indicating a correspondence between frequency components of the surface data and the frequency map.

18. A method according to claim 17, further comprising:

comparing the frequency components of the surface data with the frequency map; and indicating in case a correspondence is detected between at least one frequency of the set of function deviation indicating frequencies of the frequency map and at least one frequency component of the surface data.

19. A computer program product loadable into the internal memory of a computer, comprising software code portions for performing the method of claim 17, when run on a computer.

20. A computer program product according to claim 19, wherein the computer program product comprises a carrier.

21. A method of configuring a frequency map of a memory comprising a set of function deviation indicating frequencies, the memory being comprised in a device for indicating a function deviation of one or more details of manufacturing equipment, the method comprising:

investigating function deviation indicating frequencies occurring in the manufacturing equipment; and inputting relevant function deviation indicating frequencies into the memory.

22. A method for indicating a function deviation of one or more details of manufacturing equipment using frequency component analysis for analyzing deviations between a nominal product shape and an actual product shape of a product using surface data of a physical surface describing the actual product shape, the product having been processed by the manufacturing equipment, the analysis being based on the surface data and a set of function deviation indicating frequencies corresponding to frequencies at which function deviations occur in the one or more details, the function deviation indicating frequencies being comprised in a frequency map, the method comprising:

receiving the surface data;

performing a Fourier transformation of the surface data;

comparing frequency components of the surface data with the frequency map; and indicating in case a correspondence is detected between at least one frequency of the set of function deviation indicating frequencies of the frequency map and at least one frequency component of the surface data.

* * * * *

UNITED STATES PATENT AND TRADEMARK OFFICE
CERTIFICATE OF CORRECTION

PATENT NO. : 6,708,128 B2
DATED : March 16, 2004
INVENTOR(S) : Olle Bankeström et al.

It is certified that error appears in the above-identified patent and that said Letters Patent is hereby corrected as shown below:

<u>Title page,</u>
Item [30], Foreign Application Priority Data, please add -- Swedish Application No. 0101984-3 filed May 31, 2001 --

Signed and Sealed this

Thirteenth Day of July, 2004

JON W. DUDAS
*Acting Director of the United States Patent and Trademark Office*